United States Patent [19]

Yang

[11] Patent Number: 6,150,565

[45] Date of Patent: Nov. 21, 2000

[54] PROCESS USING $CF_2I_2$ AND OLEFINS FOR PRODUCING DIIODO FLUOROCOMPOUNDS, AND PRODUCTS THEREOF

[75] Inventor: Zhen-Yu Yang, Wilmington, Del.

[73] Assignee: E. I. du Pont de Nemours and Company, Wilmington, Del.

[21] Appl. No.: 09/142,463

[22] PCT Filed: May 14, 1997

[86] PCT No.: PCT/US97/08166

§ 371 Date: Sep. 8, 1998

§ 102(e) Date: Sep. 8, 1998

[87] PCT Pub. No.: WO97/44300

PCT Pub. Date: Nov. 27, 1997

Related U.S. Application Data

[60] Provisional application No. 60/018,087, May 22, 1996.

[51] Int. Cl.[7] .............................. C07C 43/11; C07C 19/08
[52] U.S. Cl. ......................... 568/615; 570/134; 570/137; 570/172
[58] Field of Search ............................ 568/615; 570/134, 570/137, 172

[56] References Cited

U.S. PATENT DOCUMENTS

| | | | |
|---|---|---|---|
| 2,551,639 | 5/1951 | Feasley et al. | 260/653 |
| 4,243,770 | 1/1981 | Tatemoto et al. | 525/331 |
| 4,361,678 | 11/1982 | Tatemoto et al. | 528/374 |
| 5,504,248 | 4/1996 | Krusic | 562/849 |

FOREIGN PATENT DOCUMENTS

| | | | |
|---|---|---|---|
| 926411 | 5/1963 | United Kingdom . | |
| WO 97/30957 | 8/1997 | WIPO | C07C 17/093 |

OTHER PUBLICATIONS

Elsheimer et al., Difluorodiiodomethane: its prep . . . free–radical reactions, J. Org. Chem., 49(1), 205–7., 1984. No month provided.

Sloan et al., Free Radical Addition to Olefins.,*J. Chem. Soc.*, 15, pp. 1841–1845, Apr., 1975.

Dolbier, Jr. et al., New Zinc Difluorocarbenoid Reagent, *J. Org. Chem.*, 55, pp. 5420–5422, 1990. No month provided.

Yang et al., *Ring–Opening Reactions of Fluorocyclopropanes with Halogens: A General and Useful Route to 1,3–Dihalofluoropropane Derivatives*, J. American Chemical Society, pp. 5397–5398, vol. 117, 1995. No month provided.

Elsheimer et al., *Difluorodiiodomethane: Its Preparation, Properties, and Free–Radical Reactions*, J. Org. Chem., 49, pp. 205–207, 1984. No month provided.

J. Balague et al., *Synthesis of fluorinated telomers. Part 1, Telomerization of vinylidene fluoride with perfluoroalkyl iodides*, Journal of Fluorine Chemistry, 70, pp. 215–223, 1995. No month provided.

*Primary Examiner*—Johann Richter
*Assistant Examiner*—Rosalynd Keys

[57] ABSTRACT

A process is disclosed for making diiodofluorinated compounds of the formula $ICF_2(A)_nI$ wherein n is an integer of at least 1 and each A is CXYCQZ wherein each X, Y, Q, and Z are each independently selected from the group consisting of H, F, Cl, $R_F$ and $OR_F$, and $R_F$ is a perfluoroalkyl group or perfluorinated polyether group wherein one or more of the fluorines is optionally replaced by a substituent selected from the group consisting of chlorine, bromine, iodine, hydrogen, sulfonyl fluoride, nitrile, ester, acyl chloride and acyl fluoride. The process involves reacting an olefin of the formula CXY=CQZ with $CF_2I_2$ at a temperature in the range of from about 120° C. to 240° C.

Diiodofluorinated compounds of the formula $ICF_2CH_2CHR_FI$ are also disclosed.

15 Claims, No Drawings

PROCESS USING CF$_2$I$_2$ AND OLEFINS FOR PRODUCING DIIODO FLUOROCOMPOUNDS, AND PRODUCTS THEREOF

This application is a national filing under 35 USC 371 of International Application No. PCT/US97/08166 filed May 14, 1997 and claims priority of U.S. Provisional Application Ser. No. 60/018,087 filed May 22, 1996.

FIELD OF THE INVENTION

This invention relates to diiodofluorinated compounds and their production, and more particularly to using CF$_2$I$_2$ and olefinic compounds as reactants for producing diiodofluorinated compounds.

BACKGROUND

Diiodoperfluoroalkanes are useful as chain transfer reagents for fluoroelastomers and in the free radical polymerization of fluorinated vinyl monomers. See U.S. Pat. Nos. 4,243,770 and 4,361,678. The reaction of CF$_2$I$_2$ with olefins allows the stepwise addition to the chain, thereby providing controlled chain growth. The production of these diiodoperfluoroalkanes at relatively high yields has been hampered in the past by the lack of a method by which to produce relatively high yield and purity CF$_2$I$_2$. However, as described in commonly held U.S. patent application Ser. No. 60/012,160, filed Feb. 23, 1996, a priority document listed for PCT International Publication No. WO 97/30957, CF$_2$I$_2$ can be produced in sufficiently high yields to facilitate the reactions described below.

Commonly held U.S. Pat. No. 5,504,248 describes the production of diiodofluoroalkanes by reacting I$_2$ with hexafluorocyclopropane. This process involves a relatively complex ring-opening reaction, and uses relatively expensive starting materials.

Elsheimer, et al., J. Org. Chem. 1984, 49, pp. 205–207, discloses reactions of CF$_2$I$_2$ with hydrocarbon olefins to produce iododifluoroalkenes viaphotolysis, or diiododifluoroalkanes via reactions catalyzed by peroxide at temperatures less than 100° C. The use of peroxides to form the diiododifluoroalkanes could result in the production of other reaction products, which would have to be separated from the desired products, thus adding an additional step, as well as the associated costs involved with such purification.

Many citations are found throughout the literature describing diiodofluorinated compounds, but interest continues in developing new, efficient processes for producing selected diiodofluorinated compounds.

SUMMARY OF THE INVENTION

A process is provided for making diiodofluorinated compounds of the formula ICF$_2$(A)$_n$I wherein n is an integer of at least 1 and each A is CXYCQZ wherein each X, Y, Q, and Z are each independently selected from the group consisting of H, F, Cl, R$_F$ and OR$_F$, and R$_F$ is a perfluoroalkyl group containing 1 to 20 carbon atoms or a perfluorinated polyether group containing from 2 to 20 carbon atoms wherein one or more of the fluorines of said perfluoroalkyl or perfluorinated polyether group is optionally replaced by a substituent selected from the group consisting of chlorine, bromine, iodine, hydrogen, sulfonyl fluoride, nitrile, ester, acyl chloride and acyl fluoride. The process comprises reacting an olefin of the formula CXY=CQZ with CF$_2$I$_2$ at a temperature in the range of from about 120° C. to 240° C.

Diiodofluorinated compounds of the formula ICF$_2$CH$_2$CHR$_F$I, where RF is as indicated above, are also provided in accordance with this invention.

DETAILED DESCRIPTION

This invention provides a process by which CF$_2$I$_2$ is reacted with olefins to produce diiodofluorinated compounds, generally described in Equation (I) below:

$$CF_2I_2 + CXY=CQZ \rightarrow ICF_2(A)_nI \qquad (I)$$

In Equation (I), A represents (CXYCQZ), and X, Y, Q and Z are each independently H, F, Cl, R$_F$ or OR$_F$, and preferably at least one of X, Y, Q and Z is F. The number of repeat units of A, as represented by n in Equation (I) is 1 or greater and is preferably from 1 to about 5, more preferably from 1 to 3. Of note are embodiments where n is 1; embodiments where n is 2; and embodiments where n is 3.

The process represented by Equation (I) takes place at an elevated temperature. It has been found in accordance with this invention that when conducted at temperatures of about 120° C. or above, the reaction needs no chemical catalyst or initiator to proceed. Indeed, the process of this inveniton is typically conducted in the substantial absence of a catalyst or initiator. By "substantial absence of catalyst or initiator" is meant that the reaction would effectively proceed even in the absence of any catalyst or initiator which might be added. By "catalyst or initiator" is meant materials or chemicals such as, for example, peroxides or azo compounds, which have been previously required to produce diiodofluorinated compounds at lower temperatures.

The temperature range is generally between about 120° C. and about 240° C., and is preferably between about 170° C. and about 190° C. The process can take place in the liquid or gas phase. Liquid phase reactions may be conducted in solution in inert solvents such as, for example, fluorocarbons, fluorochlorocarbons and hydrofluorocarbons, or (preferably) may be conducted neat. Although not necessary, if the reaction is carried out in the liquid state, moderate agitation is preferred. It is also preferred that oxygen and water are excluded from the reaction, and it may be convenient to carry out the reaction under an inert gas blanket, such as nitrogen.

Pressure is not critical, autogenous pressure (of all the ingredients) being generally the convenient operation pressure. Typically, the reaction is conducted at pressure within the range of from about 20 psi (about 138 Pa) to about 1000 psi (about 6900 Pa). Non-limiting examples of reaction vessels include shaker tubes, tanks, autoclaves and reactors.

It is noted that for each addition of olefinic starting material, the unit A can have either of two orientations, with either carbon involved with the olefinic bond, attaching to the end carbon of the iodo reactant. Accordingly, where the carbons involved with the olefinic bond are differently substituted, the addition of each A group can result in either of two products. Thus for example, when n is 1, the reaction can be represented as:

$$CF_2I_2 + CXY=CQZ \rightarrow ICF_2CXYCQZI + ICF_2CQZCXYI \qquad (II)$$

When X, Y and Z are each H in Equation (II), the reaction may be represented by Equation (III) below:

$$CF_2I_2 + CH_2{=}CHQ \longrightarrow ICF_2CH_2CHIQ + ICF_2CHQCH_2I \quad (III)$$
$$\phantom{CF_2I_2 + CH_2{=}CHQ \longrightarrow} \; 1 \phantom{xxxxxxxxxxx} 4 \phantom{xxxxxx} 5$$

Both fluorinated or non-fluorinated olefins, as determined by the composition of Q, give relatively good yields of adducts. When reacted with ethylene, a relatively higher yield of adduct 4 is obtained, as described in Example 1 below. A mixture of regioisomers 4 and 5 is, however, formed with propylene and vinyl fluoride (Examples 2 and 8, respectively). Fluoroalkyl substituted olefins or fluorinated polyether subsstituted olefin such as $CH_2{=}CHRF$ where RF is highly fluorinated (Examples 3 and 4) also undergo an addition reaction with $CF_2I_2$ to give 4 exclusively. Examples of highly fluorinated RF groups include $CF_2CF_2Br$, $CF_2CF_2I$, and perfluoroalkyl groups (e.g., $C_4F_9$, $C_6F_{13}$ and $C_8F_{17}$ groups).

Preferably at least one of X, Y, Z and Q is F. When X and Y are each F in Equation (I), the reaction may be represented by Equation (IV) below:

$$CF_2I_2 + CF_2{=}CZQ \longrightarrow ICF_2CF_2CIQZ + ICF_2CZQCF_2I \quad (IV)$$
$$\phantom{CF_2I_2 + CF_2{=}CZQ \longrightarrow} \; 1 \phantom{xxxxxxxxxxx} 6 \phantom{xxxxxx} 7$$

Of note are embodiments of Equation (IV) where Q is F, H, RF or ORF and embodiments where Z is F. Fluorinated olefins such as $CF_2{=}CFH$, $CF_2{=}CFCF_3$ and $CF_2{=}CH_2$ give mixtures of regioisomers 6 and 7. Unlike other perfluoroalkyl iodides, $CF_2I_2$ cleanly adds to perfluorovinyl ethers of the formula $CF_2{\equiv}CFOR_F$ to give compound 6 (Q=ORF), along with small amounts of compound 7 (Q=OR$_F$). The functional groups such as ester, sulfonyl fluoride and nitrile in the vinyl ethers do not interfere with the addition reaction, so that various functional diiodocompounds may be prepared, as found in Examples 12–15. When the reaction mixture of fluorovinyl ethers and $CF_2I_2$ is subjected to prolonged heating, as in Examples 12 and 15, the initially formed compound 6, in Equation (V) below, where Q=ORF, decomposes to $ICF_2CF_2COF$ and $R_FI$ (see also U.S. Pat. No. 5,504,248).

$$ICF_2CF_2CFIOR_F \longrightarrow ICF_2CF_2COF + R_FI \quad (V)$$
$$\phantom{xxxxx} 6$$

The addition of $R_FI$ to tetrafluoroethylene (TFE), as shown in Example 5, gives a broad distribution of telomers. See also Chemistry of Organic Fluorine Compounds, 2nd Ed. M. Hudlicky, 1992, p. 420–427). While $CF_2I_2$ reacts with TFE, the main product is a 1:1 adduct ($ICF_2CF_2CF_2I$) with only small amounts of 1:2 adduct ($I(CF_2)_5I$) and trace of 1:3 adduct ($I(CF_2)_7I$), as shown in Equation (VI) below:

$$CF_2I_2 + CF_2{=}CF_2 \longrightarrow ICF_2CF_2CF_2I + I(CF_2)_5I + I(CF_2)_7I \quad (VI)$$
$$\phantom{xxxxx} 1$$

When $CF_2{=}CFCl$ is reacted with $CF_2I_2$, a mixture of 1:1 and 1:2 adducts is formed, as shown in Equation (VII) below, where n=2.

$$CF_2I_2 + CF_2{=}CFCl \rightarrow ICF_2CF_2CFClI + ICF_2(CF_2CFCl)_2 I \quad (VII)$$

Other higher homologs are also formed (e.g., n is 3, 4, etc.). In general, higher ratios of olefinic starting materials to $CF_2I_2$ yield higher telomers (i.e., n is higher). The degree of telomerization is limited by product solidification.

Preferably, the ratio of olefinic starting material to $CF_2I_2$ is from about 1:1 to 5:1.

The diiodocompounds formed by the instant process, when one of X, Y, Z or Q is a functional group as represented by RF or ORF, may be used to chain extend or graft the resulting polymer onto another polymer, or to react to form a specific chain end which may act to change the polymer's surface properties. One example of this would be the production of a potential surfactant material when RF is a fluorinated ester or fluorinated sulfonyl group.

Compounds provided by this invention include compounds where each A is ($CH_2CHR_F$). Of note are compounds of this type having the formula $ICF_2CH_2CHR_FI$.

In the Examples below. unless otherwise specified, all reagents were used as received from Aldrich Chemical Co., Milwaukee, Wis. $CF_2I_2$ was made according to the procedure as described in co-pending U.S. patent application Ser. No. 60/012,160.

Gas chromatography (GC) was performed on an HP 5890 II Plus gas chromatograph (Hewlett Packard, Wilmington, Del.), using a 20% OV-210 column (Supelco, Bellefonte, Pa.), with an initial temperature of 50° C., a final temperature of 250° C., and a rate of 15° C./min. The $_1H$ and $^{19}F$ nuclear magnetic resonance (NMR) data were obtained using a GE Plus NMR spectometer (General Electric, Schenectady, N.Y.). All measurements are relative to deuterated chloroform ($CDCl_3$). Ratios given are those for peak areas by GC or molar ratios based on NMR data as designated in the specific examples. High resolution mass spectrometry (HRMS) was done using a Micromass-7070H (VG Analytical, Manchester, UK).

The reaction products were obtained by distillation, and their boiling points (bp, ° C.) were obtained. Elemental analyses were obtained by routine methods.

The following abbreviations are used in the Examples below:

s=singlet NMR peak
d=doublet NMR peak
t=triplet NMR peak
m=multiplet NMR peak

EXAMPLE 1

Reaction of $CF_2I_2$ with Ethylene

A 75 mL of shaker tube was charged with 30.5 g of $CF_2I_2$ and cooled to −78° C. The tube was evacuated and then 4.0 g of ethylene was added. After the tube was heated at 185° C. for 5 hour, 30.3 g of crude product was obtained which was distilled to give 27.3 g of adduct with 100% GC purity, bp 94–95° C./50 mmHg. $^{19}F$ NMR: −39.1 (t, J=14.3 Hz); $^1H$ NMR: 3.21 (t, J=7.3 Hz, 2H), 2.95 (m, 2H). HRMS: calcd for $C_3H_4F_2I_2$: 331.8371. Found: 331.8336. Anal: calcd for $C_3H_4F_2I_2$: C, 10.86; H, 1.21; F, 11.45; I, 76, 48. Found: C, 10.84; H, 1.25; F, 11.59; I, 75.96.

EXAMPLE 2

Reaction of $CF_2I_2$ with Propylene

A 75 mL of shaker tube was charged with 30.5 g of $CF_2I_2$ and cooled to −78° C. The tube was evacuated and then 5.0 g of propylene was added. After the tube was heated at 185° C. for 5 hour, 31.6 g of crude product was obtained which was distilled to give 28.7 g of product, bp 106–107° C./4.8 mmHg. GC and NMR indicated a mixture of $ICF_2CH_2CHICH_3$ and $ICH_2CH(CF_2I)CF_3$ in a ratio of 13 to 1. $^{19}F$ NMR: for major product: −35.4 (ddd J=173 Hz, J=18.4 Hz, J=8.7 Hz, 1F), −38.3 (dt, J=173 Hz, J=16.4 Hz, 1F). 1H NMR: 4.35 (m, 1H), 3.28 (m, 1H), 2.90 (m, 1H), 2.00 (d, J=7.0 Hz. 3H). HRMS: calcd for $C_4H_7F_2I_2$: 345.8527. Found: 345.8565 for $ICF_2CH_2CHICH_3$ and 345.8510 for $ICH_2CH(CF_2I)CH_3$. Anal: calcd for $C_4H_7F_2I_2$: C, 13.89; H, 1.75; F, 10.98; I, 73.38. Found: C, 13.99; H, 1.98; F, 10.80; I, 73.34.

EXAMPLE 3

Reaction of $CF_2I_2$ with 4-bromo-3,3,4,4-tetrafluorobutene-1

A 75 mL of shaker tube was charged with 30.5 g of $CF_2I_2$ and 21.0 g of $BrCF_2CF_2CH=CH_2$ and cooled to −78° C. The tube was evacuated and then heated at 180° C. for 2.5 hour. 31.6 g of crude product was obtained which was washed with aqueous $Na_2SO_3$ solution and distilled to give 28.7 g of $ICF_2CH_2CHICF_2CF_2Br$, bp 53° C./19 mmHg. $^{19}F$ NMR: −36.7 (ddd, J=176.1 Hz, J=16.2 Hz, J=7.1 Hz, 1F), —39.7 (dt, J=176 Hz, J=15.8 Hz, 1F), −59.9 (dd, J=178.6 Hz, J=7.6 Hz, 1F), −61.0 (dd, J=178.6 Hz, J=5.6 Hz, 1F), −94.6 (dt, J=260.6 Hz, J=7.2 Hz, 1F), −109.8 (ddd, J=261.0 Hz, J=18 Hz, J=7.4 Hz, 1F).

EXAMPLE 4

Reaction of $CF_2I_2$ with 4-iodo-3,3,4,4-tetrafluorobutene-1

A 75 mL of shaker tube was charged with 42.3 g of 1:1 mixture of $CF_2I_2$ and $ICF_2CF_2CH=CH_2$ and cooled to −78° C. The tube was evacuated and then heated at 180° C. for 2.5 hour. 36 g of crude product was obtained, which was washed with aqueous $Na_2SO_3$ solution and distilled to give 23.5 g of $ICF_2CH_2CHICF_2CF_2I$, bp 118–120° C./10 mmHg. $^{19}F$ NMR: −36.7 (ddd, J=175.5 Hz, J=16.0 Hz, J=7.7 Hz, 1F), −39.6 (dt, J=175.5 Hz, J=16.0 Hz, 1F), −54.8 (ddt, J=202.2 Hz, J=7.3 Hz, J=2.3 Hz, 1F), −56.0 (dd, J=203.0 Hz, J=7.0 Hz, 1F), −88.3 (dt, J=261.0 Hz, J=7.0 Hz, 1F), −106.2 (ddd, J=261.0 Hz, J=19 Hz, J=8.4 Hz, 1F).

EXAMPLE 5

Reaction of $CF_2I_2$ with Tetrafluoroethylene

A 400 mL of shaker tube was charged with 152 g of $CF_2I_2$ and cooled to −78° C. After the tube was evacuated and then heated to 185° C., 20 g of TFE was added and the tube kept at 185° C. for 2 hours. Additional 20 g of TFE was added and the tube was kept for 2 hours. Finally, 10 g of TFE was added and the tube kept for 6 hours. 192.3 g of crude products were obtained and GC indicated that a mixture of 82% $I(CF_2)_3I$ and 7% $I(CF_2)_5I$. Distillation gave 169.6 g of $I(CF_2)_3I$ with 2.5% of $I(CF_2)_5I$, bp 76–80° C./150 mmHg, and 13.1 g of high boiling residue containing 20% $I(CF_2)_3I$, 70% $I(CF_2)_5I$ and 5% $I(CF_2)_7I$. $^{19}F$ NMR for $I(CF_2)_3I$: −58.2 (t, J=4.7 Hz, 4F), −105.2 (t, J=4.7 Hz, 2F); for $I(CF_2)_5I$: −59.4 (t, J=4.6 Hz, 4F), −113.6 (s, 4F), −120.6 (m, 2F).

EXAMPLE 6

Reaction of $CF_2I_2$ with Trifluoroethylene

A 75 mL of shaker tube was charged with 30.5 g of $CF_2I_2$ and cooled to −78° C. The tube was evacuated and then 16.0 g of trifluoroethylene was added. After the tube was heated at 185° C. for 10 hour, GC indicated 70% of conversion and 26.3 g of crude product was obtained which was washed with aqueous $Na_2SO_3$ solution and distilled to give 1.5 g of 55% pure of adduct, 2.5 g of 84% pure adduct and 12.8 g of pure product bp 83° C./80 mmHg. $^{19}F$ NMR and GC indicated a mixture $ICF_2CHFCF_2I$ and $ICF_2CF_2CHFI$ in a ratio of 1.5 to 1. $^{19}F$ NMR: $ICF_2CHFCF_2I$: −52.6 (dm, J=207.8 Hz, 2F), −54.8 (dm, J=207.8 Hz, 2F), −176.2 (m, 1F); $ICF_2CF_2CHFI$: −57.9 (dm, J=207.8 Hz, 1F), −59.8 (dt, J=207.8 Hz, J=6.5 Hz, 1F), −101.0 (ddt, J=273.1 Hz, J=32.3 Hz, J=6.3 Hz, 1F), −116.3 (dm, J=273.1 Hz, 1F), −165.7 (m, 1F). HRMS: calcd. for $C_3HF_5I_2$: 385.8088. Found: 385.8023. Anal: calcd for $C_3HF_5I_2$: C, 9.34; H, 0.26; F, 24.62; I, 65.78. Found: C, 9.25; H, 0.27; F, 24.39; I, 65, 81.

EXAMPLE 7

Reaction of $CF_2I_2$ with Vinylidene Fluoride

A 75 mL of shaker tube was charged with 30.5 g of $CF_2I_2$ and cooled to −78° C. The tube was evacuated and then 10.0 g of $CF_2=CH_2$ was added. After the tube was heated at 185° C. for 8 hour, GC indicated 10% $CF_2I_2$ and 79.5% of adduct (area ratio). 35.1 g of crude products were obtained which was distilled to give 4.1 g of 50% pure of adduct and 26.4 g of pure adduct, bp 80–81° C./60 mmHg. $^{19}F$ NMR and GC indicated a mixture $ICF_2CH_2CCF_2I$ and $ICF_2CF_2CH_2I$ in a ratio of 27.6 to 1. $^{19}F$ NMR: $ICF_2CH_2CF_2I$: −39.6 (m); $ICF_2CF_2CH_2I$: −59.6 (t, J=4 Hz, 2F), −101.5 (t, J=16.4 Hz, 2F). HRMS: Calcd for $C_3H_2F_4I_2$: 367.8182. Found: 367.8168 for $ICF_2CH_2CF_2I$; 367.8150 for $ICF_2CF_2CH_2I$. Anal: calcd for $C_3H_2F_4I_2$: C, 9.80; H, 0.55; I, 69.00. Found: C, 9.76; H, 0.62; I, 68.48.

EXAMPLE 8

Reaction of $CF_2I_2$ with vinyl fluoride

A 75 mL of shaker tube was charged with 30.5 g of $CF_2I_2$ and cooled to −78° C. The tube was evacuated and then 6.0 g of vinyl fluoride was added. After the tube was heated at 185° C. for 5 hour, GC indicated 90% of conversion and 27.8 g of crude product was obtained which was distilled to give 4.9 g of 55% pure of adduct and 17.1 g of pure product, bp 87–89° C./50 mmHg. $^{19}F$ NMR and GC indicated a mixture $ICF_2CH_2CCFHI$ and $ICF_2CFHCH_2I$ in a ratio of 8.6 to 1. $^{19}F$ NMR: $ICF_2CH_2CHFI$: −37.6 (dm, J=178.5 Hz, 1F), −40.33 (dm, J=178.5 Hz, 1F), −144.7 (m, 1F); $ICF_2CFHCH_2I$: −51.8 (ddd, J=195.5 Hz, J=21.0 Hz, J=7.4 Hz, 1F), −56.3 (ddd, J=196 Hz, J=21.7 Hz, J=7.3 Hz, 1F), −176.8 (m, 1F). HRMS: calcd for $C_3H_3F_3I_2$: 349.8280. Found: 349.8391 for $ICF_2CH_2CFHI$; 349.8307 for $ICF_2CFHCH_2I$. Anal: calcd for $C_3H_3F_3I_2$: C, 10.30; H, 0.86. Found: C, 10.26; H, 1.00.

EXAMPLE 9

Reaction of $CF_2I_2$ with Hexafluoropropylene

A 75 mL of shaker tube was charged with 45.6 g of $CF_2I_2$ and cooled to −78° C. The tube was evacuated and then 24.0 g of hexafluoropropylene was added. After the tube was heated at 185° C. for 12 hour, GC indicated 55% of conversion and 40.1 g of crude were washed with aqueous $Na_2SO_3$ solution and then distilled to give 6.2 g of 82% pure of $CF_2I_2$, 2.7 g of a mixture of 60% of $CF_2I_2$ and 28% of $ICF_2CF_2CFICF_3$, bp 40–63° C./95 mmHg, 3.0 g of a mixture of 23% of $CF_2I_2$ and 62% of $ICF_2CF_2CFICF_3$, bp 64–71° C./95 mmHg and 10.6 g of 93% pure $ICF_2CF_2CFICF_3$, bp 74–76° C./95 mmHg. HRMS: calcd for $C_4F_8I_2$: 453.7962. Found: 453.7915 for $ICF_2CF_2CFICF_3$; 3452.7967 for $(ICF_2)_2CFCF_3$.

EXAMPLE 10

Reaction of $CF_2I_2$ with perfluoromethyl vinyl ether

A 75 mL of shaker tube was charged with 30.5 g of $CF_2I_2$ and cooled to $-78°$ C. The tube was evacuated and then 22.0 g of perfluoromethyl vinyl ether was added. After the tube was heated at 185° C. for 3.5 hour, GC indicated 76% of conversion and 37.2 g of crude products were distilled to give 13.8 g of 47.6% of $CF_2I_2$ and 46.7% of adduct, bp 50–79° C./100 mmHg and 18.4 g of 99% pure adduct, bp 87–89° C./50 mmHg. $^{19}$F NMR and GC indicated a mixture $ICF_2CF_2CFIOCF_3$ and $(ICF_2)_2CFOCF_3$ in a ratio of 12 to 1. $^{19}$F NMR for $ICF_2CF_2CFIOCF_3$: $-55.0$ (dm, J=204.1 Hz, 1F), $-55.3$ (d, J=11.3 Hz, 3F), $-58.4$ (ddm, J=205 Hz, J=26.4 Hz, -F), $-68.0$ (m, 1F), $-102.6$ (dt, J=276.2 Hz, J=7.7 Hz, 1F), $-104.2$ (dt, J=276.4 Hz, J=7.2 Hz, 1F); for $(ICF_2)_2OCF_3$: $-51.7$ (m, 3F), $-53.9$ (m, 4F), $-124.2$ (m, 1F); HRMS: calcd for $C_4F_8I_2O$: 469.7911. Found: 469.7930 for $ICF_2CF_2CFIOCF_3$; 469.7967 for $(ICF_2)_2CFOCF_3$.

EXAMPLE 11

Reaction of $CF_2I_2$ with perfluoropropyl vinyl ether

A 75 mL of shaker tube was charged with 30.5 g of $CF_2I_2$ and cooled to $-78°$ C. The tube was evacuated and then 60.0 g of perfluoropropyl vinyl ether was added. After the tube was heated at 185° C. for 3.5 hour, 78.5 g of crude products were distilled to give 29.0 g of perfluoropropyl vinyl ether; 6.2 g of 72% pure of adduct, bp 30–80° C./40 mmHg; 27.6 g of pure adduct, bp 83–84° C./40 mmHg; and 4.4 g of 68% pure adduct, bp 85° C./40 mmHg to 74° C./15 mmHg. Yield 79%. $^{19}$F NMR and GC indicated a mixture $ICF_2CF_2CFIOCF_2CF_2CF_3$ and $(ICF_2)_2CFOCF_2CF_2CF_3$ in a ratio of 85.4 to 13.6. $^{19}$F NMR for $ICF_2CF_2CFIOCF_2CF_2CF_3$: $-55.3$ (d, J=204.6 Hz, 1F), $-58.8$ (ddd, J=204.6 Hz, J=27 Hz, J=6.3 Hz, 1F), $-68.7$ (m, 1F), $-81.3$ to $-81.9$ (m, 4F), $-90.7$ (d, J=147.6 Hz, 1F), $-102.4$ (dt, J=276.7 Hz, J=8 Hz, 1F), $-104.4$ (dt, J=276.6 Hz, J=7.5 Hz, 1F), $-130.4$ (s, 2F). $(ICF_2)_2OCF_2CF_2CF_3$: $-53.8$ (m, 4F), $-79.4$ (m, 2F), $-81.3$ (M, 3F), $-122.3$ (m, 1F), $-129.3$ (M, 2F). HRMS: calcd for $C_6F_{12}I_2O$: 569.7847. Found: 442.8824 for $ICF_2CF_2CFIOCF_2CF_2CF_3$—I; 569.7796 for $(ICF_2)_2CFOCF_2CF_2CF_3$. Anal: calcd for $C_6F_{12}I_2O$: C, 12.65; I, 44.55. Found: C, 12.72; I, 44.23.

EXAMPLE 12

Reaction of $CF_2I_2$ with $CF_2$=$CFOCF_2CF(CF_3)$ $OCF_2CF_2CO_2Me$

A 240 mL of shaker tube was charged with 30.5 g of $CF_2I_2$ and 60.0 g of $CF_2$=$CFOCF_2CF(CF_3)OCF_2CF_2CO_2Me$ and cooled to $-78°$ C. After being evacuated at $-78°$ C., the tube was heated at 185° C. for 3.5 hour. 82.2 g of a mixture of 5% of $ICF_2CF_2COF$, 4% of $CF_2I_2$, 31% of $CF_2$=$CFOCF_2CF(CF_3)OCF_2CF_2CO_2Me$, 9% $ICF_2CF(CF_3)OCF_2CF_2CO_2Me$ and 51% adduct were obtained (GC area). Distillation gave 12.3 g of mainly $CF_2$=$CFOCF_2CF(CF_3)OCF_2CF_2CO_2Me$, bp 40–88° C./60 mmHg, 8.6 g of material containing 45% $CF_2$=$CFOCF_2CF(CF_3)OCF_2CF_2CO_2Me$ and 55% of $ICF_2CF(CF_3)OCF_2CF_2CO_2Me$, bp 82° C./50 mmHg to 102° C./4 mmHg, and 45.9 g of adduct, bp 103–110° C./3 mmHg. The adduct was a mixture of $ICF_2CF_2CFIOCF_2CF(CF_3)OCF_2CF_2CO_2Me$ and $(ICF_2)_2CFOCF_2CF(CF_3)OCF_2CF_2CO_2Me$.

EXAMPLE 13

Reaction of $CF_2I_2$ with $CF_2$=$CFOCF_2CF(CF_3)$ $OCF_2CF_2CN$

A 240 mL of shaker tube was charged with 30.5 g of $CF_2I_2$ and 45.0 g of $CF_2$=$CFOCF_2CF(CF_3)OCF_2CF_2CN$ and cooled to $-78°$ C. After being evacuated at $-78°$ C., the tube was heated at 185° C. for 4 hour. 67.8 g of crude products were obtained. Distillation gave 15 g of mainly $CF_2$=$CFOCF_2CF(CF_3)OCF_2CF_2CN$, bp 85–100° C., 37.6 g of adduct, bp 115–116° C./30 mmHg. The adduct was a mixture of $ICF_2CF_2CFIOCF_2CF(CF_3)OCF_2CF_2CN$ and $(ICF_2)_2CFOCF_2CF(CF_3)OCF_2CF_2CN$ in a ratio of 5.7 to 1. $^{19}$F NMR for $ICF_2CF_2CFIOCF_2CF(CF_3)OCF_2CF_2CN$: $-55.5$ (d, J=205.2 Hz, 1F), $-58.9$ (ddd, J=205.5 Hz, J=27.3 Hz, J=6.0 Hz, 1F), $-69.4$ (m, 1F), $-79.1$ to $-80.4$ (m, 4F), $-84.1$ to $-85.2$ (m, 2F), $-90.0$ (dm, J=152.5 Hz, 1F), $-102.0$ (dm, J=277.7 Hz, 1F), $-104.5$ (dm, J=277.7 Hz, 1F), $-108.6$ (m, 2F), $-145.1$ (t, J=21.2 Hz, 0.5F), $-145.6$ (t, J=21.3, Hz, 0.5F); for $(ICF_2)_2CFOCF_2CF(CF_3)OCF_2CF_2CN$: $-53.1$ m, 2F), $-54.5$ (m, 2F), $-78.2$ (m, 2F), $-80.1$ (m, 3F), $-84.1$ (m, 2F), $-108.4$ (m, 2F), $-121.2$ (m, 1F), $-144.6$ (m, 1F). HRMS: Calcd for $C_9F_5I_2NO_2$—I, 565.8734. Found: 565.8716 (M$^+$–I). Anal: calcd for $C_9F_{15}I_2NO_2$: C, 15.60; N, 2.02; I, 36.63. Found: C, 16.26; N, 2.02; I, 35.74.

EXAMPLE 14

Reaction of $CF_2I_2$ with $CF_2$=$CFOCF_2CF(CF_3)$ $OCF_2CF_2SO_2F$

A 240 mL of shaker tube was charged with 30.5 g of $CF_2I_2$ and 50.0 g of $CF_2$=$CFOCF_2CF(CF_3)OCF_2CF_2SO_2F$ and cooled to $-78°$ C. After being evacuated at $-78°$ C., the tube was heated at 185° C. for 4 hour. 71.3 g of crude products were obtained. Distillation gave 10.3 g of $CF_2I_2$, 42 g of adduct, 95–97° C./5.4 mmHg. The adduct was a mixture of $ICF_2CF_2CFIOCF_2CF(CF_3)OCF_2CF_2SO_2F$ and $(ICF_2)_2CFOCF_2CF(CF_3)OCF_2CF_2SO_2F$ in a ratio of 5.2 to 1. $^{19}$F NMR for $ICF_2CF_2CFIOCF_2CF(CF_3)OCF_2CF_2SO_2F$: +45.3 (m, 1F), $-55.6$ (d, J=204.7 Hz, 1F), $-58.9$ (ddd, J=204.7 Hz, J 27.2 Hz, J=6.3 Hz, 1F), $-69.3$ (m, 1F), $-79.3$ to $-80.2$ (m, 4F), $-89.8$ (dm, J=144.3 Hz, 1F), $-101.9$ (dm, J=277.9 Hz, 1F), $-104.6$ (dt, J=277.8 Hz, J=7.7 Hz, 1F), $-112.2$ (m, 2F), $-145.4$ (m, 1F); for $(ICF_2)_2CFOCF_2CF(CF_3)OCF_2CF_2SO_2F$: $-53.2$ (m, 2F), $-54.5$ (m, 2F), $-78.2$ (m, 2F), $-80.1$ (m, 5F), $-112.4$ (m, 2F), $-121.2$ (m, 1F), $-144.6$ (m, 1F).

EXAMPLE 15

Reaction of $CF_2I_2$ with $CF_2$=$CFOCF_2CF(CF_3)$ $OCF_2CF_2SO_2F$ at High Temperature A 240 mL of shaker tube was charged with 30.6 g of $CF_2I_2$ and 50.0 g of $CF_2$=$CFOCF_2CF(CF_3)OCF_2CF_2SO_2F$ and cooled to $-78°$ C. After being evacuated at $-78°$ C., the tube was heated at 185° C. for 4 hour and 240° C. for 8 hours. 71.5 g of crude products were obtained. GC indicated a mixture of $ICF_2CF_2COF$, $ICF_2CF(CF_3)OCF_2CF_2SO_2F$, and $(ICF_2)_2CFOCF_2CF(CF_3)OCF_2CF_2SO_2F$ in a ratio of 4.1:6.6:1 (area ratio). Distillation gave 12.6 of 93% pure $ICF_2CF_2COF$, bp 58–63° c, 6.0 g of a mixture of $ICF_2CF_2COF$ and $ICF_2CF(CF_3)OCF_2CF_2SO_2F$, bp 26–100° C./200 mmHg, 17.9 g of $ICF_2CF(CF_3)OCF_2CF_2SO_2f$, bp 100–102° C./200 mm hg, 16.7 g of a mixture of 75% $ICF_2CF(CF_3)OCF_2CF_2SO_2F$ and 16% $(ICF_2)_2CFOCF_2CF(CF_3)OCF_2CF_2SO_2F$ and 4.3 g of $(ICF_2)_2CFOCF_2CF(CF_3)OCF_2CF_2SO_2F$. $^{19}$F NMR for $ICF_2CF(CF_3)OCF_2CF_2SO_2F$: +45.5 (m, 1f), $-58.7$ (dm, J=213.7 hz, 2F), $-60.0$ (dm, J=214 Hz, 2F), $-76.9$ (m, 3F), $-77.9$ (dd, J=139.2 Hz, J=22.7 Hz, 1F), $-79.7$ (dm, J=139.2 Hz, 1F), $-122.2$ (s, 2f), $-133.6$ (m, 1F).

What is claimed is:

1. A process for making diiodofluorinated compounds of the formula $ICF_2(A)_nI$; wherein n is 1, A is $CH_2CHR_F$ and $R_F$ is a perfluoroalkyl group containing 1 to 20 carbon atoms or a perfluorinated polyether group containing from 2 to 20 carbon atoms wherein one or more of the fluorines of said perfluoroalkyl or perfluorinated polyether group is optionally replaced by a substituent selected from the group consisting of chlorine, bromine, iodine, sulfonyl fluoride, nitrile, ester, acyl chloride and acyl fluoride, comprising:

reacting an olefin of the formula $CH_2=CHR_F$ with $CF_2I_2$ at a temperature in the range of from about 120° C. to 240° C.

2. The process of claim 1 wherein the temperature is between about 170° C. and about 190° C.

3. A process for making diiodofluorinated compounds of the formula $ICF_2(A)_nT$ wherein n is an integer of at least 1 and each A is $CF_2CQF$ wherein each Q is independently selected from the group consisting of F, Cl, R, and $OR_F$, and $R_F$ is a perfluoroalkyl group containing 1 to 20 carbon atoms or a perfluorinated polyether group containing from 2 to 20 carbon atoms wherein one or more of the fluorines of said perfluoroalkyl or perfluorinated polyether group is optionally replaced by a substituent selected from the group consisting of chlorine, bromine, iodine, hydrogen, sulfonyl fluoride, nitrile, ester, acyl chloride and acyl fluoride, comprising reacting an olefin of the formula $CF_2=CQF$ with $CF_2I_2$ at a temperature in the range of from about 120° C. to 240° C. in the absence of catalyst or initiator.

4. The process of claim 3 wherein n is 1to 5.

5. The process of claim 3 wherein n is 1 to 3.

6. The process of claim 3 wherein n is 1.

7. The process of claim 3 wherein the olefin is $CF_2=CFCF_3$.

8. The process of claim 3 wherein the olefin is $CF_2=CF_2$ or $CF_2=CFCl$.

9. A diiodofluorinated compound of formula:

$$ICF_2CH_2CHR_FI$$

wherein $R_F$ is a perfluoroalkyl group containing 1 to 20 carbon atoms or a perfluorinated polyether group containing from 2 to 20 carbon atoms wherein one or more of the fluorines of said perfluoroalkyl or perfluorinated polyether group is optionally replaced by a substituent selected from the group consisting of chlorine, bromine, iodine, sulfonyl fluoride, nitrile, ester, acyl chloride and acyl fluoride.

10. The diiodofluorinated compound of claim 9 having the formula $ICF_2CH_2CH(CF_2CF_2Br)I$.

11. The diiodofluorinated compound of claim 9 having the formula $ICF_2CH_2CH(CF_2CF_2I)I$.

12. The process of claim 1 wherein the reaction is conducted in the substantial absence of catalyst or initiator.

13. The process of claim 3 wherein the olefin is a perfluorovinylether of the formula $CF_2=CFOR_F$.

14. A process for making diiodofluorinated compounds of the formula $ICF_2(A)_nI$ wherein n is 1, A is $CF_2CFOR_F$ and $R_F$ is a perfluoroalkyl group containing 1 to 20 carbon atoms or a perfluorinated polyether group containing from 2 to 20 carbon atoms wherein one or more of fluorines of said perfluoroalkyl or perfluorinated polyether group is optionally replaced by a substituent selected from the group consisting of chlorine, bromine, iodine, hydrogen, sulfonyl fluoride, nitrile, ester, acyl chloride and acyl fluoride, comprising:

reacting an olefin of the formula $CF_2=CFOR_F$ with $CF_2I_2$ at a temperature in the range of from about 120° C. to 240° C.

15. The process of claim 14 wherein the reaction is conducted in the substantial absence of catalyst or initiator.

* * * * *